US006770876B2

(12) United States Patent
Gu et al.

(10) Patent No.: US 6,770,876 B2
(45) Date of Patent: Aug. 3, 2004

(54) MASS SPECTROMETER AUTOSAMPLER

(75) Inventors: Ming Gu, Yardley, PA (US); Wenjeng Li, Plainsboro, NJ (US); John W. Allen, Eastampton, NJ (US)

(73) Assignee: Bristol-Myers Squibb Company, Princeton, NJ (US)

(*) Notice: Subject to any disclaimer, the term of this patent is extended or adjusted under 35 U.S.C. 154(b) by 0 days.

(21) Appl. No.: 10/412,191

(22) Filed: Apr. 11, 2003

(65) Prior Publication Data

US 2003/0222007 A1 Dec. 4, 2003

Related U.S. Application Data

(60) Provisional application No. 60/371,886, filed on Apr. 11, 2002.

(51) Int. Cl.[7] .............................................. B01D 15/08
(52) U.S. Cl. .................... 250/288; 73/61.59; 210/198.2
(58) Field of Search .......................... 210/143, 70, 656, 210/657, 658, 659, 635, 198.2, 91; 422/63, 65, 81, 101; 435/164, 309.1; 436/164, 161; 23/239, 233; 73/23.43, 61.56, 42.6, 23.41, 69.59, 69.52, 69.55, 69.68, 61.62, 863; 91/101, 105; 141/130; 250/281, 282, 288

(56) References Cited

U.S. PATENT DOCUMENTS

| | | | |
|---|---|---|---|
| 3,546,946 A | | 12/1970 | Smith |
| 3,609,040 A | * | 9/1971 | Kuzel et al. ................... 422/64 |
| 3,918,913 A | | 11/1975 | Stevenson et al. |
| 3,960,003 A | | 6/1976 | Beyer et al. |
| 4,166,094 A | * | 8/1979 | Froehlich et al. ......... 73/864.25 |
| 5,601,707 A | * | 2/1997 | Clay et al. ................ 210/198.2 |
| 5,721,384 A | * | 2/1998 | Tanihata ................... 73/864.81 |
| 5,738,783 A | * | 4/1998 | Shirota et al. ............ 210/198.2 |

OTHER PUBLICATIONS

Figeys, D. et al., "Identification of proteins by capillary electrophoresis—tandem mass spectrometry: Evaluation of an on–line solid–phase extraction device", Journal of Chromatography A, vol. 763, pp. 295–306 (1997).

Figeys, D. et al., "Optimization of solid phase microextraction—capillary zone electrophoresis—mass spectrometry for high sensitivity protein identification", Electrophoresis, vol. 19, pp. 2338–2347 (1998).

Naylor, S. et al., "Membrane Preconcentration—Capillary Electrophoresis—Mass Spectrometry in the Analysis of Biologically Derived Metabolites and Biopolymers", Biomedical Chromatography, vol. 10, pp. 325–330 (1996).

Shelly, D.C. et al., "Dead–Volume Free Termination for Packed Columns in Microcapillary Liquid Chromatography", Anal. Chem., vol. 56, pp. 2990–2992 (1984).

Haynes et al, "Proteome profiling—pitfalls and progress", Yeast 2000, 17:81–87.

Yates et al., "Sequencing Peptides Derived from the Class II Major Histocompatibility Complex by Tandem Mass Spectrometry", Cell Biology, pp. 380–388.

* cited by examiner

Primary Examiner—John R. Lee
Assistant Examiner—James P. Hughes
(74) Attorney, Agent, or Firm—Keith R. Lange

(57) ABSTRACT

The present invention relates to an autosampler device useful in high pressure liquid chromatography (HPLC), and more particularly to a device useful for the automated introduction of small sample volumes into a HPLC system. Methods of analyzing low abundant protein samples using such a device are also included.

43 Claims, 4 Drawing Sheets

MASS SPECTROMETER AUTOSAMPLER

This application claims the benefit of provisional U.S. application Ser. No. 60/371,886, filed Apr. 11, 2002, which is incorporated herein by reference in its entirety.

FIELD OF THE INVENTION

The present invention relates to a method and apparatus useful in high pressure liquid chromatography (HPLC), and more particularly to an autosampler device useful for the automated introduction of small sample volumes into a HPLC system.

BACKGROUND OF RELATED TECHNOLOGY

It is desirable to identify low abundant proteins from biological samples in order to investigate the role of individual proteins in biological processes, such as in the field of proteomics. It is further desirable to develop sensitive analytical methods which provide not only the means to analyze extremely low abundant proteins but also the possibility to reduce or avoid costly and time-consuming protein enrichment processes.

One such method involves the use of HPLC. Generally, HPLC requires that a molecular species to be separated and analyzed is dissolved in liquid (the mobile phases), and then conveyed by those liquids through a stationary phase. In the stationary phase, a large surface area is presented which is in intimate contact with the mobile phases. Mixtures of analyte compounds, dissolved in the mobile phases, can be separated. The differential retention causes the analytes to elute from the column with respect to time. The eluting analytes will typically transit through an in-line detector, where quantitative and/or qualitative examination of analytes will occur. Such examination is typically performed using a mass spectrometer (MS). In recent years, the use of MS with capillary electrophoresis (CE) or liquid chromatography (LC) has become increasingly popular for analyzing low abundance proteins.

A key element in the successful analysis of low abundant proteins is to ensure that an entire protein digest at about 20 $\mu$l is injected into a capillary column with minimum sample loss. CE has been demonstrated to inject the volume of protein digest by constructing a segment of solid phase extraction material (Figeys, et al., *J. Chromatogr. A.*, 763:295–306 (1997); Figeys, et al., *Electrophoresis*, 19:2338–47 (1998)) or a piece of membrane (Naylor, et al. al., *J. Biomed. Chromatogr.*, 10:325–30 (1996)) for sample enrichment and subsequently eluting the protein digest for separation and MS analysis. On the other hand, capillary LC loads the protein digest directly into a capillary column by a pressurized sample introduction device (Shelly, et al., *Analytical Chemistry*, 56:2990–2 (1984)). While both CE/MS and capillary LC/MS achieve excellent detection limits for protein analysis, the capillary LC/MS approach is more robust, and therefore more widely used for analysis of low abundant proteins than the CE/MS method.

Known devices used for low abundant protein analysis by capillary LC/MS generally consist of a cylinder and a top cover and are capable of accommodating only one sample. Although such devices are capable of delivering a sample into a capillary LC column, the whole sample introduction procedures are manually driven and tedious. For example, in order to introduce a sample, an operator must open a stainless steel cylinder to place a sample vial in, fasten bolts through a cover, and pressurize the cylinder for sample introduction. As these operations are off line, the operator also needs to depressurize the device after loading, remove the column from the cylinder, and put the column on a LC/MS system for analysis. As a result, it is impossible to perform automated data acquisition for analysis of a batch of samples using such devices.

Known devices for automated capillary LC sampling have numerous disadvantages for analysis of low abundant proteins. For example, in order to introduce a sample volume of 20 $\mu$l into the capillary column, it is often necessary to have up to 50 $\mu$l of sample in the sample vial. As a result of this sample waste, such devices are not optimized for identifying low abundant proteins efficiently.

Accordingly, a need exists for a device useful for automated capillary LC sampling which overcomes these problems. The present invention is directed to meeting these and other needs.

SUMMARY OF THE INVENTION

Figure 1:
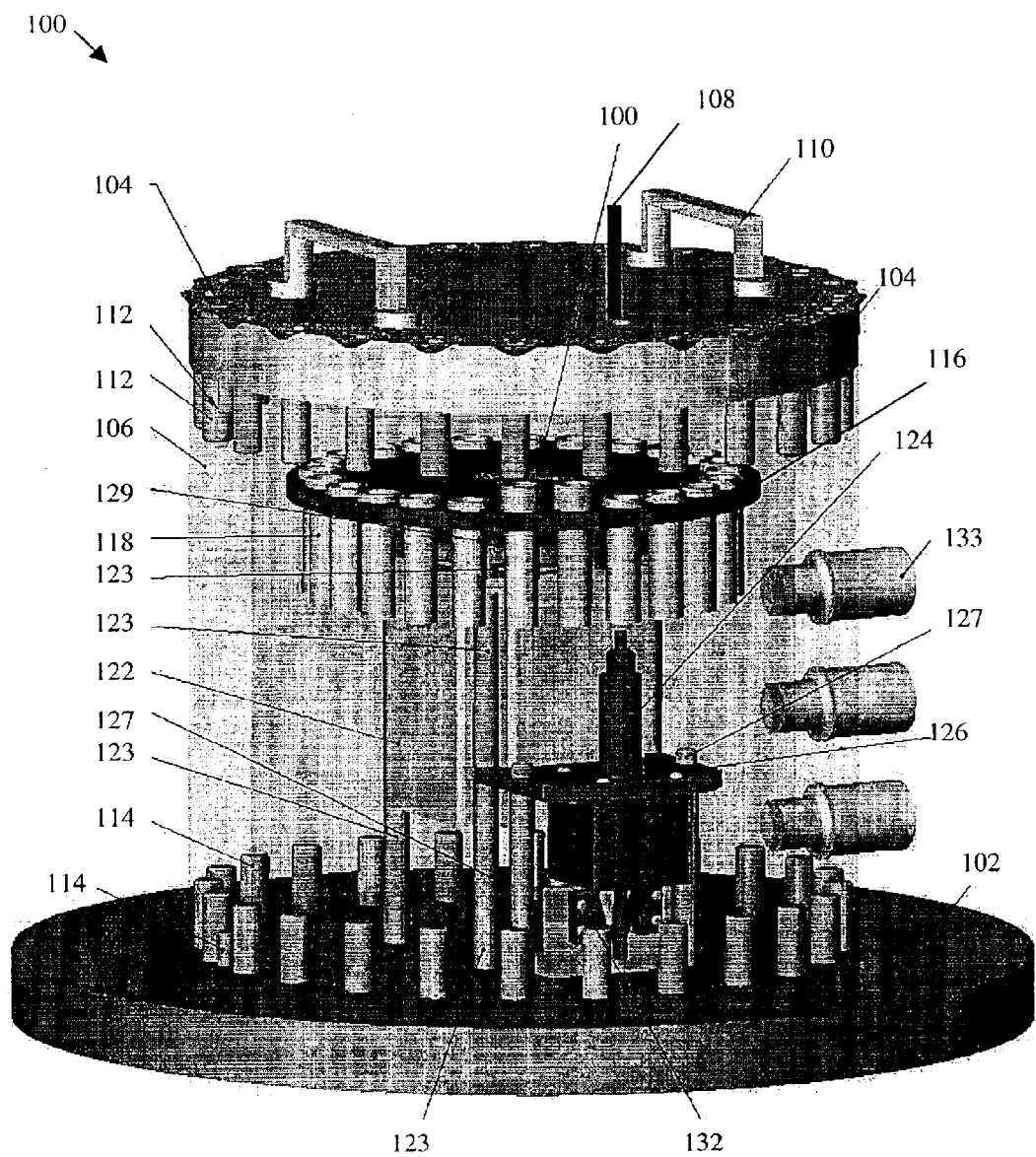
FIG. 1 shows an autosampler of the present invention.

The present invention relates to a method and apparatus useful in high pressure liquid chromatography (HPLC), and more particularly to an autosampler device useful for the automated introduction of small sample volumes into a HPLC system.

In one aspect, the present invention is directed to an autosampler device for introducing a test sample into a HPLC system. The autosampler device includes a housing which has at least two surfaces; one or more apertures defined by the housing which are each for receiving capillary tubing; a plate member within the housing which defines at least one opening for receiving a test sample container; a first movement member (such as a motor) which is fixedly attached at a first side thereof to the housing and at a second side thereof to the plate member, and which is for moving the plate member; a second movement member (such as a solenoid) which is fixedly attached to the housing, and which is for moving a vial positioned within said test sample container; and at least one inlet passageway in fluid communication with the housing, and which is for introducing a fluid material into the housing.

The housing substantially defines a cylinder and includes a first surface, a second surface and a wall member connecting the first surface and the second surface. The first surface defines a cover member in removable sealing registry over the wall member, and the second surface defines a base member in fixed sealing registry under the wall member. The inventive autosampler device permits substantially an entire test sample present in the vial to be introduced into the capillary tubing, and is useful for the analysis of low abundant protein samples. The autosampler device permits from about 50 percent to about 100 percent, from about 55 percent to about 100 percent, from about 60 percent to about 100 percent, from about 65 percent to about 100 percent, from about 70 percent to about 100 percent, from about 75 percent to about 100 percent, from about 80 percent to about 100 percent, from about 85 percent to about 100 percent, from about 90 percent to about 100 percent, and from about 95 percent to about 100 percent of the test sample present in the vial to be introduced into the capillary tubing.

At least one of the first movement member and the second movement member are controlled by one or more electronic devices, such as computing devices. The computing devices permit substantially automated operation of the autosampler device. The fluid material is a gaseous material, such as nitrogen, and effects a pressure increase in the housing. The pressure increase causes a test sample present in the vial to be introduced into capillary tubing. The second movement member causes the vial to be disposed about, and contact, the capillary tubing. The first movement member is for moving the plate member in a substantially circumferential manner, and the second movement member is for moving the test sample container in a substantially vertical direction. The autosampler device also includes a sensor for determining when the test sample container is aligned with the capillary tubing.

In another aspect, the present invention is directed to a system for introducing a test sample into a HPLC system. This system includes the autosampler device described above, and a pressurizing system in fluid communication with the inlet passageway of the autosampler device. This system is useful for the analysis of low abundant protein samples. The pressurizing system is a two-stage pressurizing system.

In another aspect, the present invention is directed to a HPLC system, which includes the autosampler device described above, a pressurizing system in fluid communication with the inlet passageway of the autosampler device, and a mass spectrometer. The mass spectrometer is cooperative with the capillary tubing of the autosampler device. The HPLC system is useful for the analysis of low abundant protein samples.

In another aspect, the present invention is directed to a method for analyzing a low abundant protein sample, which includes the steps of (a) introducing a low abundant protein sample into the autosampler device described above, and (b) acquiring data related to the low abundant protein sample.

DETAILED DESCRIPTION OF THE INVENTION

The present invention is directed to an automated sampling device useful in a capillary liquid chromatography/mass spectrometry (LC/MS) system, as well as to a LC/MS system employing such a device. The present invention permits substantially entire sample volumes present in a sample vial to be introduced into a capillary column. The present invention is further directed to methods for analyzing biological samples, such as proteins, peptides, metabolites, and other low abundant molecular species, using such a device and system.

Accordingly, the present invention is well-suited for analyzing low-abundant proteins. The present invention is further suited for use in an electronically-controlled environment for performing automated micro-scale protein analysis of batch samples. Particularly, through the use of inventive pressurized sample introduction means, the present invention permits the analysis of substantially entire test samples which are introduced into the device.

Turning to FIG. 1, an automated sampling device 100 of the present invention is shown. Automated sampling device 100 consists of a housing which comprises a base member 102 connected to a cover member 104 by a wall member 106 (shaded). Base member 102, cover member 104 and wall member 106 desirably define a cylinder, and cover member 104 is in removable sealing registry with wall member 106. One of skill in the art will recognize that the housing member may be of any shape or size which permits its operation within the scope of the present invention. Cover member 104 defines one or more apertures, each of which is for receiving a piece of capillary tubing 108 leading to a liquid chromatography column. Cover member 104 also desirably includes a handle 110 for facilitating removal thereof from wall member 106. Spacers 112 and 114 on cover member 104 and base member 102, respectively, permit appropriate spacing within housing 100 for operation of the autosampler.

Contained within the housing of device 100 is a plate 116 which has one or more openings, each of which is for receiving a test sample container 118. Each test sample container 118 is desirably supported by plate 116, and is capable of receiving a test sample vial 120, as shown in FIG. 2, or alternatively may directly receive a sample to be tested. Desirably, plate 116 is adapted for receiving up to 24 test sample containers, but one of skill in the art will recognize that the present invention is suitable for use with any desired number of test sample containers.

A first movement member desirably rotates plate 116 circumferentially, which permits alignment of a vial 120 with capillary tubing 108, thereby permitting subsequent introduction of a test sample present in such vial 120 into capillary tubing 108. Such first movement member is shown as a motor 122, supported by standoffs 123, but one of skill in the art will recognize that other means may be used to effect the desired movement of plate 116. An example of a motor 122 suitable for use in the present invention is a Warner Electric SLO-SYN Step Motor. Motor 122 is attached to the housing, such as by attachment on a first end to base member 102 and on a second end to plate 116. Alternatively, motor 122 may move plate 116 in a grid pattern, such as along an X-Y axis, also thereby permitting alignment of a vial 120 with capillary tubing 108. The present invention may include a single LC column or may include multiple LC columns. When a single LC column is used, it is desirable that one or more test sample containers 118 include a vial 120 having a wash solution to permit the LC column to be washed in-between each sample testing.

Figure 2A:
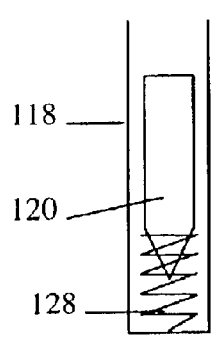
FIG. 2a shows a vial holder, vial, uncompressed spring and relative position of capillary tubing present in the inventive autosampler.
Figure 2B:
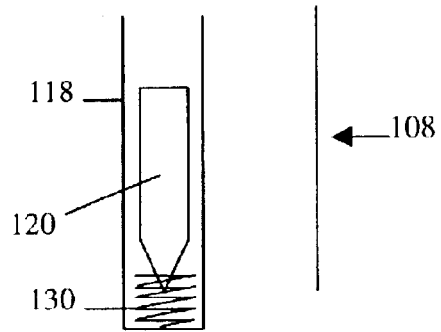
FIG. 2b shows a vial holder, vial, compressed spring and relative position of capillary tubing present in the inventive autosampler.

A second movement member is positioned beneath plate 116 for movement of test sample containers 118. The second movement member is shown as a solenoid 124, supported by a linear motor plate 126 which in turn is supported by standoffs 127, but one of skill in the art will recognize that other means may be used to effect the desired movement of sample containers 118. Solenoid 124 is desirably a linear motor with a one-inch stroke. A switcher bracket 132 is positioned beneath solenoid 124 for operation thereof. As shown in FIGS. 2a and 2b, test sample container 118 includes a spring member 128 onto which a vial 120, which includes a sample to be tested, is positioned. Once test sample container 118 is aligned with solenoid 124, solenoid 124 moves substantially vertically, thereby contacting sample container 118 and moving sample container 118 in an upwards direction, resultantly compressing spring member 130 (FIG. 2b). FIG. 2a shows the relative position of a vial 120 to capillary tubing 108 when vial 120 is resting on an uncompressed spring 128. FIG. 2b shows the relative position of a vial 120 to capillary tubing 108 when vial 120 is resting on a compressed spring 130. Desirably, compressed spring member 130 is compressed about 5 mm. The resultant force on vial 120 causes capillary tubing 108 to contact the bottom of vial 120.

Motor 122 and solenoid 124 are controlled using conventional electronic components, and are desirably under software control, in order to automate operation of device 100. Further, a sensor plate 129 is associated with plate 116 to verify alignment of plate 116 with capillary tubing 108.

In order to effect movement of a test sample from vial 120 into a LC column, device 100 is maintained under high pressure, such as about 600 psi. The use of such high pressure, in cooperation with capillary tubing 108 substantially contacting the bottom of vial 120, permits the transfer of substantially all liquid sample present in vial 120 into the LC column through capillary tubing 108. For example, when it is desired to introduce a 20 microliter sample into the LC column for analysis, an approximately 20 microliter sample need be present in vial 120.

Figure 3:
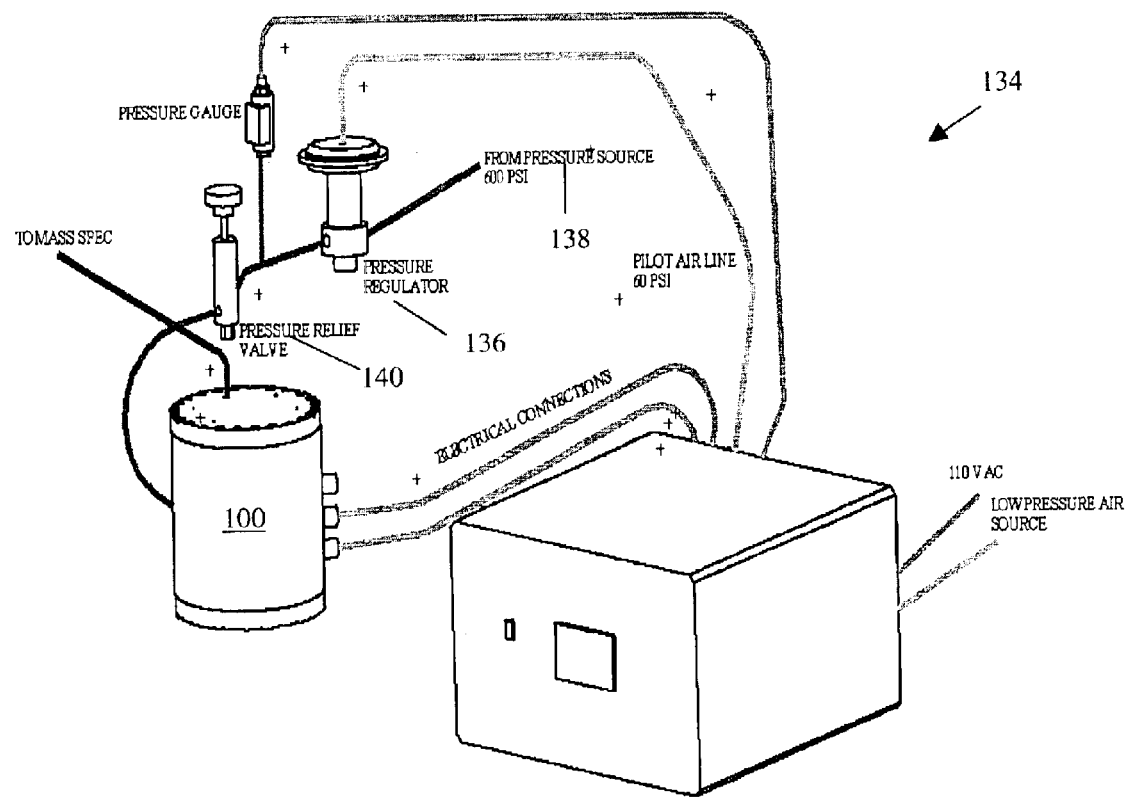
FIG. 3 shows a two-stage pressurizing system for use with the inventive autosampler.

An inlet passageway 133, in fluid communication with wall member 106, permits introduction of a fluid, desirably a gas such as nitrogen, into device 100. As shown in FIG. 3, in the present invention, a two-stage pressurizing system 134 permits the desired pressurization of device 100 without the formation of bubbles in the sample liquid being tested. The first stage of pressure is controlled by a regulator 136 from a pressure source 138. When opened, a manual switch valve on regulator 136 delivers nitrogen gas to a pressure release valve 140. Pressure release valve 140 maintains gas flow at a low flow rate to ensure that no bubbles are generated during pressurizing. Pressure release valve 140 is digitally controlled and also monitors the pressure inside device 100. When desired pressure is reached inside device 100, pressure release valve 140 is automatically turned off.

Any conventional mass spectrometer is suitable for use in the present invention, such as those manufactured by the Thermo Finnigan Corporation. Further, those skilled in the art will appreciate that the present invention may be manufactured using standard methods and materials.

EXAMPLE 1

Operation of LC/MS System with Autosampler

Figure 4:
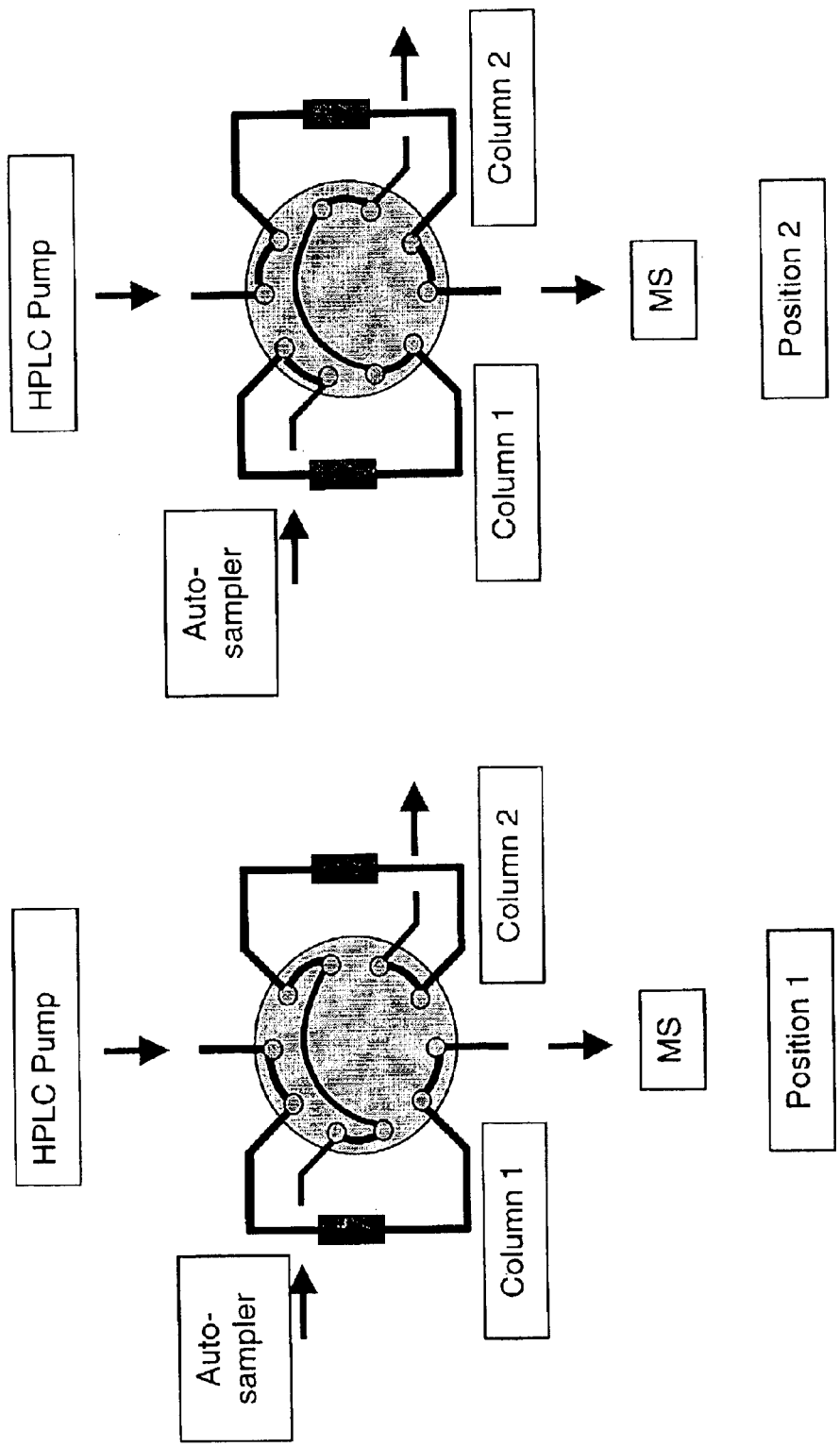
FIG. 4 shows the operation of the inventive autosampler in a micro-LC/MS system.

The inventive autosampler is integrated in a LC/MS system to enable automated analysis of low abundant proteins. One useful instrument configuration is illustrated in FIG. 4. A 10-port switching valve connects two HPLC columns, the autosampler, and the LC/MS system. The autosampler introduces sample liquid into the columns through capillary tubing connected to port 9 of the valve. Port 1 of the valve connects with HPLC pumps, while port 6 of the valve leads to a mass spectrometer. Two HPLC columns can take different flow paths at different time. This is done by programming the switching valve through mass spectrometer software. With the configuration shown, the operation of the autosampler incorporated LC/MS system allows sample introduction on one column by the autosampler and data acquisition with another column by LC/MS simultaneously.

Although the invention has been shown and described with respect to exemplary embodiments thereof, various other changes, omissions and additions in the form and detail thereof may be made therein without departing from the spirit and scope of the invention.

What is claimed is:

1. An autosampler device for introducing a test sample into a HPLC system, comprising:

a. a housing, said housing comprising at least two surfaces;
   b. one or more apertures defined by said housing, wherein said one or more apertures are each for receiving capillary tubing;
   c. a plate member within said housing, said plate member defining at least one opening for receiving a test sample container;
   d. a first movement member, wherein said first movement member is fixedly attached at a first side thereof to said housing and at a second side thereof to said plate member, and wherein said first movement member is for moving said plate member;
   e. a second movement member, wherein said second movement member is fixedly attached to said housing, and wherein said second movement member is for moving a vial positioned within said test sample container; and
   f. at least one inlet passageway in fluid communication with said housing, said inlet passageway being for introducing a fluid material into said housing.

2. The autosampler device of claim 1, wherein said first movement member is a motor.

3. The autosampler device of claim 1, wherein said second movement member is a solenoid.

4. The autosampler device of claim 1, wherein said housing comprises a first surface, a second surface and a wall member connecting said first surface and said second surface.

5. The autosampler device of claim 4, wherein said first surface defines a cover member in removable sealing registry over said wall member.

6. The autosampler device of claim 4, wherein said second surface defines a base member in fixed sealing registry under said wall member.

7. The autosampler device of claim 1, wherein said housing substantially defines a cylinder.

8. The autosampler device of claim 1, wherein said autosampler device permits substantially an entire test sample present in said vial to be introduced into said capillary tubing.

9. The autosampler device of claim 1, wherein said autosampler device is useful for the analysis of low abundant protein samples.

10. The autosampler device of claim 1, wherein said autosampler device permits from about 50 percent to about 100 percent of said test sample present in said vial to be introduced into said capillary tubing.

11. The autosampler device of claim 1, wherein said autosampler device permits from about 55 percent to about 100 percent of said test sample present in said vial to be introduced into said capillary tubing.

12. The autosampler device of claim 1, wherein said autosampler device permits from about 60 to about 100 percent of said test sample present in said vial to be introduced into said capillary tubing.

13. The autosampler device of claim 1, wherein said autosampler device permits from about 65 to about 100 percent of said test sample present in said vial to be introduced into said capillary tubing.

14. The autosampler device of claim 1, wherein said autosampler device permits from about 70 to about 100 percent of said test sample present in said vial to be introduced into said capillary tubing.

15. The autosampler device of claim 1, wherein said autosampler device permits from about 75 to about 100 percent of said test sample present in said vial to be introduced into said capillary tubing.

16. The autosampler device of claim 1, wherein said autosampler device permits from about 80 to about 100 percent of said test sample present in said vial to be introduced into said capillary tubing.

17. The autosampler device of claim 1, wherein said autosampler device permits from about 85 to about 100 percent of said test sample present in said vial to be introduced into said capillary tubing.

18. The autosampler device of claim 1, wherein said autosampler device permits from about 90 to about 100 percent of said test sample present in said vial to be introduced into said capillary tubing.

19. The autosampler device of claim 1, wherein said autosampler device permits from about 95 to about 100 percent of said test sample present in said vial to be introduced into said capillary tubing.

20. The autosampler device of claim 1, wherein at least one of said first movement member and said second movement member are controlled by one or more electronic devices.

21. The autosampler device of claim 20, wherein said one or more electronic devices are computing devices.

22. The autosampler device of claim 21, wherein said one or more computing devices permits substantially automated operation of said autosampler device.

23. The autosampler device of claim 1, wherein said fluid material is a gaseous material.

24. The autosampler device of claim 23, wherein said gaseous material is nitrogen.

25. The autosampler device of claim 1, wherein said fluid material effects a pressure increase in said housing.

26. The autosampler device of claim 25, wherein said pressure increase in said housing causes a test sample present in said vial to be introduced into said capillary tubing.

27. The autosampler device of claim 1, wherein said second movement member causes said vial to contact said capillary tubing.

28. The autosampler device of claim 1, wherein said second movement member causes said vial to be disposed about said capillary tubing.

29. The autosampler device of claim 1, wherein said first movement member is for moving said plate member in a substantially circumferential manner.

30. The autosampler device of claim 1, wherein said second movement member is for moving said test sample container in a substantially vertical direction.

31. The autosampler device of claim 1, further comprising a sensor for determining when said test sample container is aligned with said capillary tubing.

32. A system for introducing a test sample into a HPLC system, comprising:
   a. the autosampler device of claim 1; and
   b. a pressurizing system in fluid communication with said inlet passageway of the device of claim 1.

33. The system of claim 32, wherein said autosampler device is useful for the analysis of low abundant protein samples.

34. The system of claim 32, wherein said pressurizing system is a two-stage pressurizing system.

35. A system for introducing a test sample into a HPLC system, comprising:
   a. a housing, said housing comprising at least two surfaces;
   b. one or more apertures defined by said housing, wherein said one or more apertures are each for receiving capillary tubing;
   c. a plate member within said housing, said plate member defining at least one opening for receiving a test sample container;
   d. a first movement member, wherein said first movement member is fixedly attached at a first side thereof to said housing and at a second side thereof to said plate member, and wherein said first movement member is for moving said plate member;
   e. a second movement member, wherein said second movement member is fixedly attached to said housing, and wherein said second movement member is for moving a vial positioned within said test sample container;
   f. at least one inlet passageway in fluid communication with said housing, said inlet passageway being for introducing a fluid material into said housing;
   g. a pressurizing system in fluid communication with said inlet passageway.

36. The system of claim 35, wherein said system is useful for the analysis of low abundant protein samples.

37. The system of claim 35, wherein said pressurizing system is a two-stage pressurizing system.

38. A HPLC system, comprising:
   a. the autosampler device of claim 1;
   b. a pressurizing system in fluid communication with said inlet passageway of the autosampler device of claim 1; and
   c. a mass spectrometer, said mass spectrometer being cooperative with said capillary tubing of the autosampler device of claim 1.

39. The HPLC system of claim 38, wherein said autosampler device is useful for the analysis of low abundant protein samples.

40. A HPLC system, comprising:
   a. a housing, said housing comprising at least two surfaces;
   b. one or more apertures defined by said housing, wherein said one or more apertures are each for receiving capillary tubing;
   c. a plate member within said housing, said plate member defining at least one opening for receiving a test sample container;
   d. a first movement member, wherein said first movement member is fixedly attached at a first side thereof to said housing and at a second side thereof to said plate member, and wherein said first movement member is for moving said plate member;
   e. a second movement member, wherein said second movement member is fixedly attached to said housing, and wherein said second movement member is for moving a vial positioned within said test sample container;
   f. at least one inlet passageway in fluid communication with said housing, said inlet passageway being for introducing a fluid material into said housing;
   g. a pressurizing system in fluid communication with said inlet passageway; and
   h. a mass spectrometer, said mass spectrometer being cooperative with said capillary tubing.

41. The HPLC system of claim 40, wherein said HPLC system is useful for the analysis of low abundant protein samples.

42. A method for analyzing a low abundant protein sample, comprising a. introducing a low abundant protein sample into the autosampler device of claim 1, and
b. acquiring data related to said low abundant protein sample.

43. A method for analyzing a low abundant protein sample, comprising
   a. introducing a low abundant protein sample into an autosampler device, wherein said autosampler device comprises:
      i. a housing, said housing comprising at least two surfaces;
      ii. one or more apertures defined by said housing, wherein said one or more apertures are each for receiving capillary tubing;
      iii. a plate member within said housing, said plate member defining at least one opening for receiving a test sample container;
      iv. a first movement member, wherein said first movement member is fixedly attached at a first side thereof to said housing and at a second side thereof to said plate member, and wherein said first movement member is for moving said plate member;
      v. a second movement member, wherein said second movement member is fixedly attached to said housing, and wherein said second movement member is for moving a vial positioned within said test sample container;
      vi. at least one inlet passageway in fluid communication with said housing, said inlet passageway being for introducing a fluid material into said housing;
      vii. a pressurizing system in fluid communication with said inlet passageway; and
      viii. a mass spectrometer, said mass spectrometer being cooperative with said capillary tubing;
   b. acquiring data related to said low abundant protein sample.

* * * * *